United States Patent [19]

Scherschlicht et al.

[11] Patent Number: 4,496,545
[45] Date of Patent: Jan. 29, 1985

[54] NONAPEPTIDE FOR TREATING ADDICTIVE DRUG WITHDRAWAL CONDITIONS

[75] Inventors: Richard R. Scherschlicht, Inzlingen, Fed. Rep. of Germany; René Tissot, Chêne-Bourg, Switzerland

[73] Assignee: Hoffmann-La Roche Inc., Nutley, N.J.

[21] Appl. No.: 583,520

[22] Filed: Feb. 24, 1984

Related U.S. Application Data

[62] Division of Ser. No. 379,162, May 17, 1982, Published Application No. 4,444,758.

[30] Foreign Application Priority Data

May 21, 1981 [CH] Switzerland ................... 3306/81

[51] Int. Cl.$^3$ ................... A61K 37/00; C07C 103/52
[52] U.S. Cl. ................... 514/16; 260/112.5 R
[58] Field of Search ................... 424/177; 260/112.5 R

[56] References Cited

PUBLICATIONS

Experientia, vol. 33, No. 4, (1976), pp. 548–552.
Proc. Nat'l Acad. Sci., vol. 74, No. 3, (1977), 1282–1286.

Primary Examiner—Delbert R. Phillips
Attorney, Agent, or Firm—Jon S. Saxe; Bernard S. Leon; Alan R. Stempel

[57] ABSTRACT

A nonapeptide and its pharmaceutically acceptable salts are described for the treatment of addictive drug withdrawal conditions.

6 Claims, No Drawings

NONAPEPTIDE FOR TREATING ADDICTIVE DRUG WITHDRAWAL CONDITIONS

This is a division of application Ser. No. 379,162 filed May 17, 1982, now U.S. Pat. No. 4,444,758 issued 4/24/84.

BACKGROUND OF THE INVENTION

The nonapeptide of the formula

Trp-Ala-Gly-Gly-Asp-Ala-Ser-Gly-Glu    I is a compound known under the abbreviation DSIP (delta sleep inducing peptide) (see, for example, Monnier et al., Experimentia 33, 548–552 [1977] or Schoenenberger et al., Proc. Natl. Acad. Sci. USA 74, 1282–1286 [1977]), having sleep-inducing properties.

SUMMARY OF THE INVENTION

A method is described for controlling, treating or preventing addictive drug withdrawal conditions of a subject. This method comprises administering to the subject a pharmaceutically effective amount of a nonapeptide of formula I or a pharmaceutically acceptable salt thereof. Properties of this nonapeptide make it suitable for addictive drug conditions such as for example those caused by one or more pharmacologically addictive drugs known per se, such as opium alkaloids, e.g. morphine and heroin and other morphine-type compounds, opiates, barbiturates, methadone, cannabis and ethanol (as associated with alcoholism).

DETAILED DESCRIPTION OF THE INVENTION

The present invention relates to controlling, treating and preventing addictive drug withdrawal conditions by employing pharmaceutical preparations containing a compound of formula I or a pharmaceutically acceptable salt thereof.

The terms "addictive drug withdrawal conditions", as used herein are those conditions known per se relating to physiological or psychological symptoms or other effects observable or determinable medically upon abstention from drugs to which one is habituated or addicted.

An opiate-dependent organism for example reacts the same irrespective of species on the sudden withdrawal of the opiate (e.g. morphine) with withdrawal symptoms, i.e. addictive drug withdrawal conditions. In the course of this occurrence central and peripheral symptoms appear, of which the most striking in the mouse is a series of violent leaps (the so-called "jumping"). The number of leaps per time interval is proportional to the intensity of the withdrawal effect and their enumeration enables the incident to be evaluated quantitatively.

Although the preferred field of application of the nonapeptide is the treatment of dependence caused by compounds of the morphine-type (opiates and the known substitute preparations), withdrawal manifestations which are occasioned by the dependence on compounds of the barbiturate-alcohol type and of the cannabis type (classified according to the World Health Organization (WHO, 1974) can also be treated. Finally, the nonapeptide is suitable for the treatment of the nowadays common polytoxicomania.

In addition to the nonapeptide itself, its physiologically compatible salts or pharmaceutically acceptable salts (e.g. alkali metal salts or the ammonium salt) can also be used.

The novel activity of the nonapeptide can be demonstrated by the following experimental procedure in which the inhibition of the withdrawal leaps, triggered off by naloxone, of the morphine-dependent mouse is measured:

In order to produce the dependence a compressed tablet, which contained 75 mg of morphine (base) and which progressively dissolved with continuous liberation of the morphine, was implanted under the dorsal skin of male mice (weight about 22 g). On the third day after the implantation the morphine antagonist naloxone in a dosage of 0.1 mg/kg was administered subcutaneously to the animals in order to trigger off the withdrawal leaps.

After the injection, the leaps of each individual animal were counted for 20 minutes. The group median value was calculated from the total leaps of 8 animals, which formed a group. As the positive control the animals of one group received 30 mg/kg of morphine subcutaneously 30 minutes before administration of the antagonist. Two to four groups received 10 ml/kg of physiological sodium chloride solution (negative control) 2 hours before the naloxone administration intravenously. The remaining groups received DSIP in various dosages (0.01, 0.015, 0.03, 0.06 and 0.1 mg/kg, intravenously and 0.03, 0.1 and 0.3 mg/kg, subcutaneously) 2 hours before the naloxone administration. The dosage median values and, respectively, control median values were calculated from all individual values per dosage and, respectively, the positive and negative controls. The results of this experimental procedure are reproduced in Table 1.

As is evident from Table 1, the median of the negative controls (pretreatment with sodium chloride solution) lay at 160 leaps per animal within 20 minutes after naloxone administration. The median of the positive controls (pretreatment with morphine) amounted to 43 leaps per animal or 27% of the negative control. The nonapeptide DSIP lowered the median of the total leaps per animal at a dosage of 0.015 mg/kg i.v. to 126 or 79% of the negative control and at a dosage of 0.03 mg/kg i.v. to 105 leaps or 66% of the negative control. By 0.1 mg/kg s.c. the median of total leaps per animal was lowered to 138 or 86% and by 0.3 mg/kg s.c. the median was lowered to 86 or 54% of the negative control.

Toxicological studies were carried out on 12 male and 12 female rats as well as on 3 male and 3 female dogs per dosage. For this purpose DSIP was dissolved in physiological sodium chloride solution and administered intravenously daily for 4 weeks in the dosages of 0.6, 1.8 and 6 mg/kg. At an interval of 2 weeks during these studies the hematological, hematochemical and the urine status were determined, and the electrocardiogram was recorded and analyzed.

At the termination of the aforementioned studies all animals were painlessly killed and there followed the autopsy besides the removal of organ samples for histological investigations. The aforementioned dosages, which were a maximum of 50 times greater than that intended for use in human beings, were tolerated without any side effects not only by rats but also by dogs. Also, in the case of those animals which received the maximum dosage, the hematological, hematochemical and urine values lay within the physiological limits and no changes in the electrocardiogram manifested themselves. The histological analysis of about 30 organs and of the injection sites gave not the slightest evidence of damage to organs and showed that the local tolerance at the injection sites was excellent.

The results of a clinical study with 56 alcoholic or methadone- or heroin-dependent patients is compiled in Table 2. Of the 25 alcoholic patients 8 were on admission already in delirium tremens to a medium to severe degrees. After the first subjective and objective withdrawal signs manifested themselves the patients received up to 4 intravenous infusions of in each case 0.0214 mg/kg of DSIP daily. For this purpose, the substance was dissolved in physiological sodium chloride solution and infused in the course of 5 minutes.

substances). The preparations can also be lyophilizates which are brought into solution shortly before the administration.

A typical dosage unit in humans can be considered 1 mg of the active substance, which dosage can be administered once to several times daily over a more or less lengthy period (for example 1 week). A suitable daily dosage in humans is 1,5 mg per 75 kg body weight. The optimum dosage depends, however, very much on individual factors, the addictive drug as well as the degree of dependence and can vary within relatively wide limits. It is within the skill of the physician to determine an appropriate dosage in each individual case.

TABLE 1

| | | Inhibition of the withdrawal leaps in the mouse after naloxone by DSIP | | | |
|---|---|---|---|---|---|
| Substance | Dosage | Leaps/animal (median) | % of negative control | Number of animals | Number of groups |
| NaCl sol. | 10 ml · kg$^{-1}$ i.v. | 160 | 100 | 176 | 22 |
| Morphine | 30 mg · kg$^{-1}$ s.c. | 43 | 27 | 88 | 11 |
| DSIP | 0.01 mg · kg$^{-1}$ i.v. | 149 | 93 | 24 | 3 |
| " | 0.015 mg · kg$^{-1}$ i.v. | 126 | 79 | 24 | 3 |
| " | 0.03 mg · kg$^{-1}$ i.v. | 105 | 66 | 40 | 5 |
| " | 0.06 mg · kg$^{-1}$ i.v. | 148 | 93 | 24 | 3 |
| " | 0.1 mg · kg$^{-1}$ i.v. | 161 | 100 | 32 | 4 |
| " | 0.03 mg · kg$^{-1}$ s.c. | 165 | 103 | 16 | 2 |
| " | 0.1 mg · kg$^{-1}$ s.c. | 138 | 86 | 24 | 3 |
| " | 0.3 mg · kg$^{-1}$ s.c. | 86 | 54 | 16 | 2 |

TABLE 2

| | Decrease in the withdrawal symptoms of different origin by DSIP in clinical trials | | | | | |
|---|---|---|---|---|---|---|
| | Effect of DSIP (1 mg per infusion) | | | Tolerance of DSIP | | |
| Abused drug | Present | Not present | Uncertain | excellent | good | poor |
| Alcohol without delirium tremens | 14 | 3 | — | 15 | 2 | — |
| Alcohol with delirium tremens | 6 | 1 | 1 | 7 | 1 | — |
| Methadone | 10 | 3 | 2 | 14 | 1 | — |
| Heroin | 8 | 6 | 2 | 12 | 2 | 2 |
| Total number of patients | 38 | 13 | 5 | 48 | 6 | 2 |

After each of the aforementioned infusions the 38 patients responding to the treatment (see Table 2) reported a decrease in the subjectively-felt withdrawal symptoms and the clinical personnel observed a decline in the objective symptoms such as tremor, sweating, salivation and nausea. The delirium tremens was terminated by the treatment in 6 of 8 cases and did not occur in 14 to 17 cases, contrary to the clinical prognosis before the beginning of the treatment. DSIP was ineffective in 4 of the 25 cases of alcohol dependence, in 3 of the 15 cases of methadone dependence and in 6 of the 16 cases of heroin dependence. In 5 of the 56 cases a definitive statement concerning the effectiveness was not possible. The duration of treatment amounted to a maximum of 3 days. Even after this short period the patients had either fully recovered or felt only mild, slight to endurable symptoms.

The nonapeptide and its pharmaceutically acceptable or physiologically compatible salts can, therefore, be used in the form of pharmaceutical preparations, which are suitable for intravenous and subcutaneous administration, for the treatment of addictive drug withdrawal conditions or for their prevention. The preparations can contain the usual pharmaceutically acceptable carrier materials and adjuvants known per se, i.e. organic or inorganic inert carrier materials or solvents as well as other adjuvants, (e.g. preserving, stabilizing or wetting agents, salts for varying the osmotic pressure or buffer

EXAMPLE 1

A solution for injection was prepared containing:

| Nonapeptide | 1.0 mg |
|---|---|
| p-Chloro-m-cresol | 1.0 mg |
| Sodium chloride | 8.9 mg |
| Water for injection ad | 1.0 ml |

The manufacture is carried out in the following manner:

p-Chloro-m-cresol is dissolved in N$_2$-gasified water for injection at about 90° C. To this solution, cooled to room temperature, are added the nonapeptide and the sodium chloride and dissolved while stirring. The solution obtained is made up to the end volume with N$_2$-gasified water for injection, filtered through sterilized membrane filter (pore size 0.22 um) and filled into ampoules of 1 ml under aseptic conditions.

EXAMPLE 2

There were manufactured lyophilizates of solutions containing:

| Nonapeptide | 0.55 mg | 1.1 mg |
|---|---|---|
| D-Mannitol (pyrogen-free) | 10.0 mg | 10.0 mg |

| | | |
|---|---|---|
| -continued | | |
| Water for injection ad | 1.0 ml | 1.0 ml |

The manufacture was carried out in the following manner:

The nonapeptide and the mannitol are dissolved in $N_2$-gasified water for injection and the solution is made up to the calculated volume. The solution obtained is filtered through a sterile membrane filter (pore diameter 0.2 um) and 1 ml aliquots are filled under aseptic conditions into sterile 5 ml ampoules (diameter 13 mm). After the lyophilization the ampoules are sealed under $N_2$ at a pressure of 550 mbar.

The finished injection solution is obtained by dissolving the foregoing lyophylizate in 2.2 ml of 0.9% sterile NaCl solution.

What is claimed is:

1. A pharmaceutical composition comprising a nonapeptide of the formula

Trp-Ala-Gly-Gly-Asp-Ala-Ser-Gly-Glu or a pharmaceutically acceptable salt thereof in an amount between 0.55 mg and 1.1 mg and a pharmaceutically acceptable carrier for treating addictive drug withdrawal conditions in a subject.

2. A pharmaceutical composition according to claim 1 further comprising adjuvants.

3. A pharmaceutical composition according to claim 1 wherein the nonapeptide or pharmaceutically acceptable salt thereof is a lyophilizate.

4. A pharmaceutical composition according to claim 1 comprising 1.0 mg of said nonapeptide.

5. A pharmaceutical composition according to claim 1 comprising 1.0 mg of said peptide and further comprising 1.0 mg of p-chloro-m-cresol, 8.9 mg of sodium chloride and 1.0 ml of sterile water for injection.

6. A pharmaceutical composition according to claim 1 further comprising 10.0 mg of D-mannitol (pyrogen free) and 1.0 ml of sterile water for injection.

* * * * *